United States Patent
Terui

(10) Patent No.: US 12,135,397 B2
(45) Date of Patent: Nov. 5, 2024

(54) RADIATION IMAGING APPARATUS AND IMAGE ACQUISITION METHOD

(71) Applicant: CANON KABUSHIKI KAISHA, Tokyo (JP)

(72) Inventor: Kosuke Terui, Kanagawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 345 days.

(21) Appl. No.: 17/646,423

(22) Filed: Dec. 29, 2021

(65) Prior Publication Data

US 2022/0120919 A1    Apr. 21, 2022

Related U.S. Application Data

(63) Continuation of application No. PCT/JP2020/027639, filed on Jul. 16, 2020.

(30) Foreign Application Priority Data

Jul. 23, 2019   (JP) ................................ 2019-135678

(51) Int. Cl.
*G01T 1/17*      (2006.01)
*A61B 6/00*      (2024.01)
(Continued)

(52) U.S. Cl.
CPC .................. *G01T 1/17* (2013.01); *G01T 7/00* (2013.01); *H04N 5/32* (2013.01); *A61B 6/4233* (2013.01); *A61B 6/4241* (2013.01); *A61B 6/482* (2013.01)

(58) Field of Classification Search
None
See application file for complete search history.

(56) References Cited

U.S. PATENT DOCUMENTS 9,445,030 B2   9/2016   Yagi et al.
9,470,802 B2   10/2016  Okada et al.
(Continued)

FOREIGN PATENT DOCUMENTS

JP    2009-504221 A    2/2009
JP    2016-92706 A     5/2016
(Continued)

OTHER PUBLICATIONS

U.S. Appl. No. 17/652,006, Atsushi Iwashita, filed Feb. 22, 2022.

*Primary Examiner* — Edwin C Gunberg
(74) *Attorney, Agent, or Firm* — VENABLE LLP

(57) ABSTRACT

A radiation imaging apparatus includes an imaging unit having a plurality of pixels. Each of the plurality of pixels includes a conversion element configured to convert radiation into an electrical signal, a processing circuit configured to process the electrical signal output from the conversion element, and a holding unit configured to sample and hold the electrical signal output from the processing circuit. After radiation irradiation from a radiation source is started and before next radiation irradiation from the radiation source is started, the holding unit samples and holds, at a first timing and a second timing which is after the first timing, the electrical signal output from the processing circuit. A gain of the processing circuit at the first timing and the gain of the processing circuit at the second timing are different from each other.

16 Claims, 11 Drawing Sheets

(51) Int. Cl.
  *A61B 6/42* (2024.01)
  *G01T 7/00* (2006.01)
  *H04N 5/32* (2023.01)

(56) References Cited

U.S. PATENT DOCUMENTS

| | | | |
|---|---|---|---|
| 9,655,586 B2 | 5/2017 | Yagi et al. | |
| 9,737,271 B2 | 8/2017 | Iwashita et al. | |
| 9,823,363 B2 | 11/2017 | Sato | |
| 9,971,046 B2 | 5/2018 | Ryu et al. | |
| 9,980,685 B2 | 5/2018 | Iwashita et al. | |
| 9,989,656 B2 | 6/2018 | Sato et al. | |
| 10,136,868 B2 * | 11/2018 | Zou | A61B 6/4208 |
| 10,197,684 B2 | 2/2019 | Terui et al. | |
| 10,274,612 B2 | 4/2019 | Ishii et al. | |
| 10,441,238 B2 | 10/2019 | Terui et al. | |
| 10,779,777 B2 | 9/2020 | Terui et al. | |
| 10,782,251 B2 | 9/2020 | Sato et al. | |
| 11,047,808 B2 | 6/2021 | Iwashita et al. | |
| 11,047,994 B2 | 6/2021 | Terui | |
| 11,185,301 B2 | 11/2021 | Torii et al. | |
| 2008/0232549 A1 | 9/2008 | Poorter | |
| 2016/0131772 A1 | 5/2016 | Sato | |
| 2016/0270755 A1 | 9/2016 | Takenaka et al. | |
| 2019/0250284 A1 | 8/2019 | Naito | |
| 2019/0349541 A1 | 11/2019 | Iwashita et al. | |
| 2020/0150059 A1 | 5/2020 | Torii et al. | |
| 2020/0211238 A1 | 7/2020 | Iwashita et al. | |
| 2020/0245441 A1 | 7/2020 | Tsukuda et al. | |
| 2021/0041584 A1 | 2/2021 | Terui et al. | |
| 2021/0118193 A1 | 4/2021 | Torii et al. | |
| 2022/0047238 A1 | 2/2022 | Terui et al. | |

FOREIGN PATENT DOCUMENTS

| | | |
|---|---|---|
| JP | 2018-78394 A | 5/2018 |
| JP | 2019-24926 A | 2/2019 |
| WO | 2007/017773 A2 | 2/2007 |

\* cited by examiner

RADIATION IMAGING APPARATUS AND IMAGE ACQUISITION METHOD

CROSS-REFERENCE TO RELATED APPLICATIONS

This application is a Continuation of International Patent Application No. PCT/JP2020/027639, filed Jul. 16, 2020, which claims the benefit of Japanese Patent Application No. 2019-135678, filed Jul. 23, 2019, both of which are hereby incorporated by reference herein in their entirety.

BACKGROUND OF THE INVENTION

Field of the Invention

The present invention relates to a radiation imaging apparatus and an image acquisition method.

Background Art

As an imaging method using a radiation imaging apparatus, an energy subtraction method is used. The energy subtraction method is a method of processing a plurality of images obtained by performing imaging a plurality of times while changing the energy of radiation with which a subject is irradiated, thereby obtaining new images (for example, bone images and soft tissue images). The time interval to capture a plurality of radiation images is, for example, several sec or more in a radiation imaging apparatus for still image capturing, or about 100 msec in a radiation imaging apparatus for normal moving image capturing. Even in a radiation imaging apparatus for high-speed moving image capturing, the time interval is about 10 msec. If the subject moves in this time interval, an artifact occurs due to the movement. It is therefore difficult to obtain a radiation image of a fast moving subject such as a heart by the energy subtraction method.

In PTL 1, a system that performs dual energy imaging is described. In this system, at the time of imaging, the tube voltage of an X-ray source is set to a first kV value and then changed to a second kV value. When the tube voltage has the first kV value, a first signal corresponding to a first sub-image is integrated. After the integrated signal is transferred to a sample hold node, the integration is reset. After that, when the tube voltage has the second kV value, a second signal corresponding to a second sub-image is integrated. Hence, read of the integrated first signal and integration of the second signal are performed in parallel.

CITATION LIST

Patent Literature

PTL 1: Japanese Patent Laid-Open No. 2009-504221

As for the first sub-image and the second sub-image obtained by the method of PTL 1, the signal value of one sub-image may be much smaller than the signal value of the other sub-image, or much larger conversely. It may be hard to avoid such a situation depending on the imaging environment (for example, the source image distance (SID), the thickness of the subject, and the like). If the signal value of one sub-image is remarkably small, the S/N of the sub-image may lower, resulting in lowering of the accuracy of energy subtraction. If the signal amount of the sub-image is remarkably large, this may lead to output saturation of the sub-image and impede correct energy subtraction.

SUMMARY OF THE INVENTION

The present invention provides, for example, a technique advantageous in obtaining an image having satisfactory image quality.

According to one aspect of the present invention, there is provided a radiation imaging apparatus including an imaging unit having a plurality of pixels, wherein each of the plurality of pixels includes a conversion element configured to convert radiation into an electrical signal, a processing circuit configured to process the electrical signal output from the conversion element, and a holding unit configured to sample and hold the electrical signal output from the processing circuit, after radiation irradiation from a radiation source is started and before next radiation irradiation from the radiation source is started, the holding unit samples and holds, at a first timing and a second timing which is after the first timing, the electrical signal output from the processing circuit, and a gain of the processing circuit at the first timing and the gain of the processing circuit at the second timing are different from each other.

Further features of the present invention will become apparent from the following description of exemplary embodiments with reference to the attached drawings.

DESCRIPTION OF THE EMBODIMENTS

Figure 1:
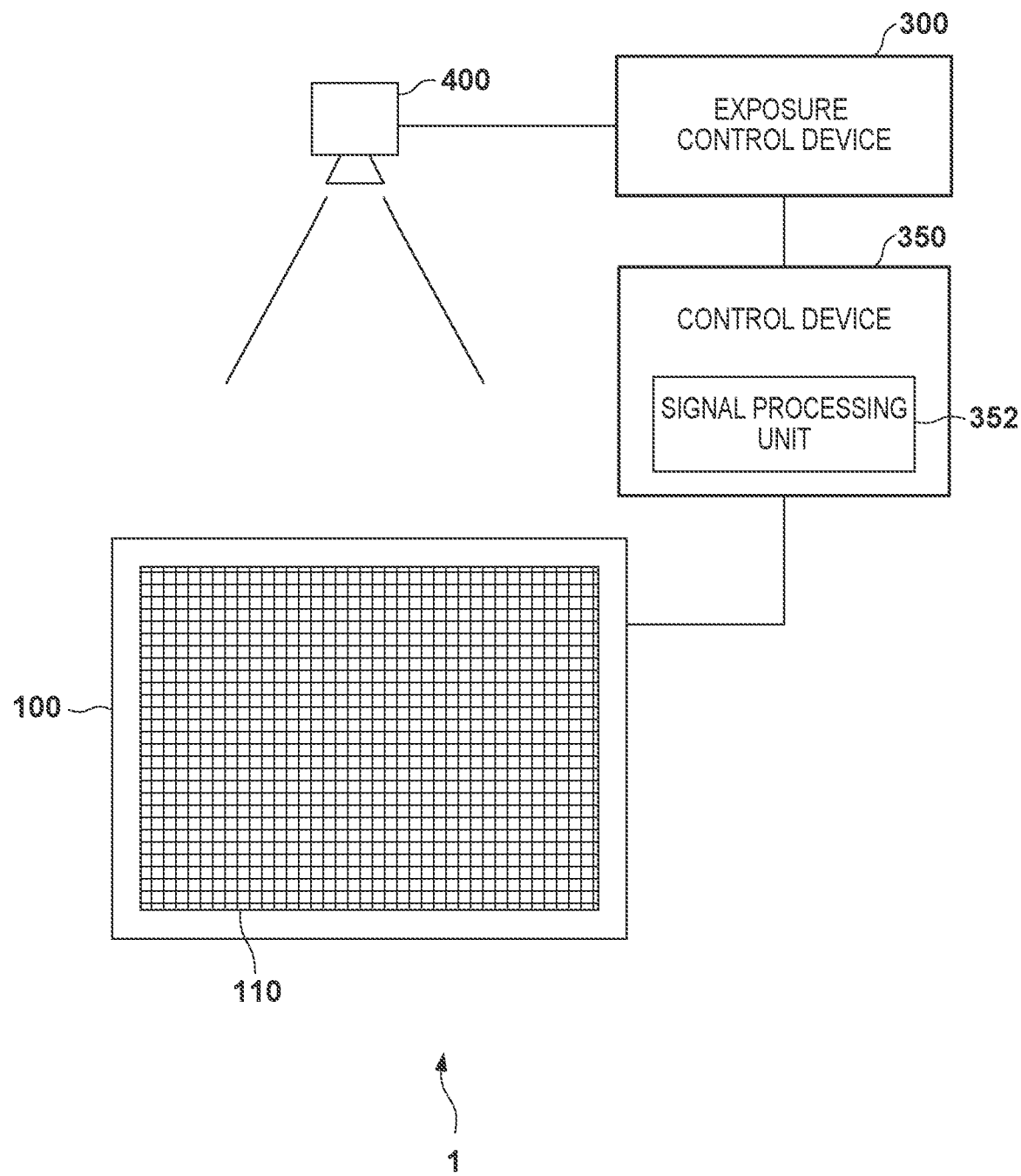
FIG. 1 is a block diagram showing the configuration of a radiation imaging apparatus according to the first embodiment of the present invention.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

FIG. 1 shows the configuration of a radiation imaging apparatus 1 according to the first embodiment of the present invention. The radiation imaging apparatus 1 can include an imaging unit 100 including a pixel array 110 with a plurality of pixels, and a signal processing unit 352 that processes a signal from the imaging unit 100. The imaging unit 100 can have, for example, a panel shape. The signal processing unit 352 may be configured as a part of a control device 350, as shown in FIG. 1, may be stored in the same housing as the imaging unit 100, or may be stored in a housing different from the imaging unit 100 and the control device 350. The radiation imaging apparatus 1 is an apparatus configured to obtain a radiation image by an energy subtraction method. The energy subtraction method is a method of processing a plurality of images obtained by performing imaging a plurality of times while changing the energy of radiation with which a subject is irradiated, thereby obtaining new radiation images (for example, bone images and soft tissue images). The term "radiation" can include, for example, α-rays, β-rays, γ-rays, particle beams, and cosmic rays in addition to X-rays.

The radiation imaging apparatus 1 can include a radiation source 400 that generates radiation, an exposure control device 300 that controls the radiation source 400, and the control device 350 that controls the exposure control device 300 (radiation source 400) and the imaging unit 100. The control device 350 can include the signal processing unit 352 that processes a signal supplied from the imaging unit 100, as described above. Some or all of the functions of the control device 350 can be incorporated in the imaging unit 100. Alternatively, some of the functions of the imaging unit 100 can be incorporated in the control device 350. The control device 350 can be formed by a computer (processor), and a memory that stores a program to be provided to the computer. The signal processing unit 352 can be formed by a part of the program. Alternatively, the signal processing unit 352 can be formed by a computer (processor), and a memory that stores a program to be provided to the computer. The control device 350 may be wholly or partially formed by a digital signal processor (DSP) or a programmable logic array (PLA). The control device 350 and the signal processing unit 352 may be designed and manufactured by a logic synthesis tool based on files that describe their operations.

The exposure control device 300 includes, for example, an exposure switch, and can cause the radiation source 400 to emit radiation when the exposure switch is turned on and also notify the control device 350 of information representing the timing of radiation emission. Alternatively, the exposure control device 300 causes the radiation source 400 to emit radiation in accordance with an instruction from the control device 350.

Radiation whose energy (wavelength) changes can be emitted in the continuous emission period of radiation from the radiation source 400. Radiation images for two energies different from each other are acquired using such radiation, and the radiation images are processed by the energy subtraction method, thereby acquiring one new radiation image.

Alternatively, the radiation source 400 may have a function of changing the energy (wavelength) of radiation. The radiation source 400 can have a function of changing the energy of radiation by, for example, changing a tube voltage (a voltage applied between the cathode and the anode of the radiation source 400).

Each of the plurality of pixels that form the pixel array 110 of the imaging unit 100 can include a conversion element that converts radiation into an electrical signal (for example, charges), a processing circuit that processes the electrical signal output from the conversion element, and a holding unit that samples and holds the electrical signal output from the processing circuit. Each conversion element may be configured to directly convert radiation into an electrical signal or may be configured to convert radiation into light such as visible light and then convert the light into an electrical signal. In the latter case, a scintillator configured to convert radiation into light can be used. The scintillator can be shared by the plurality of pixels of the pixel array 110.

Figure 2:
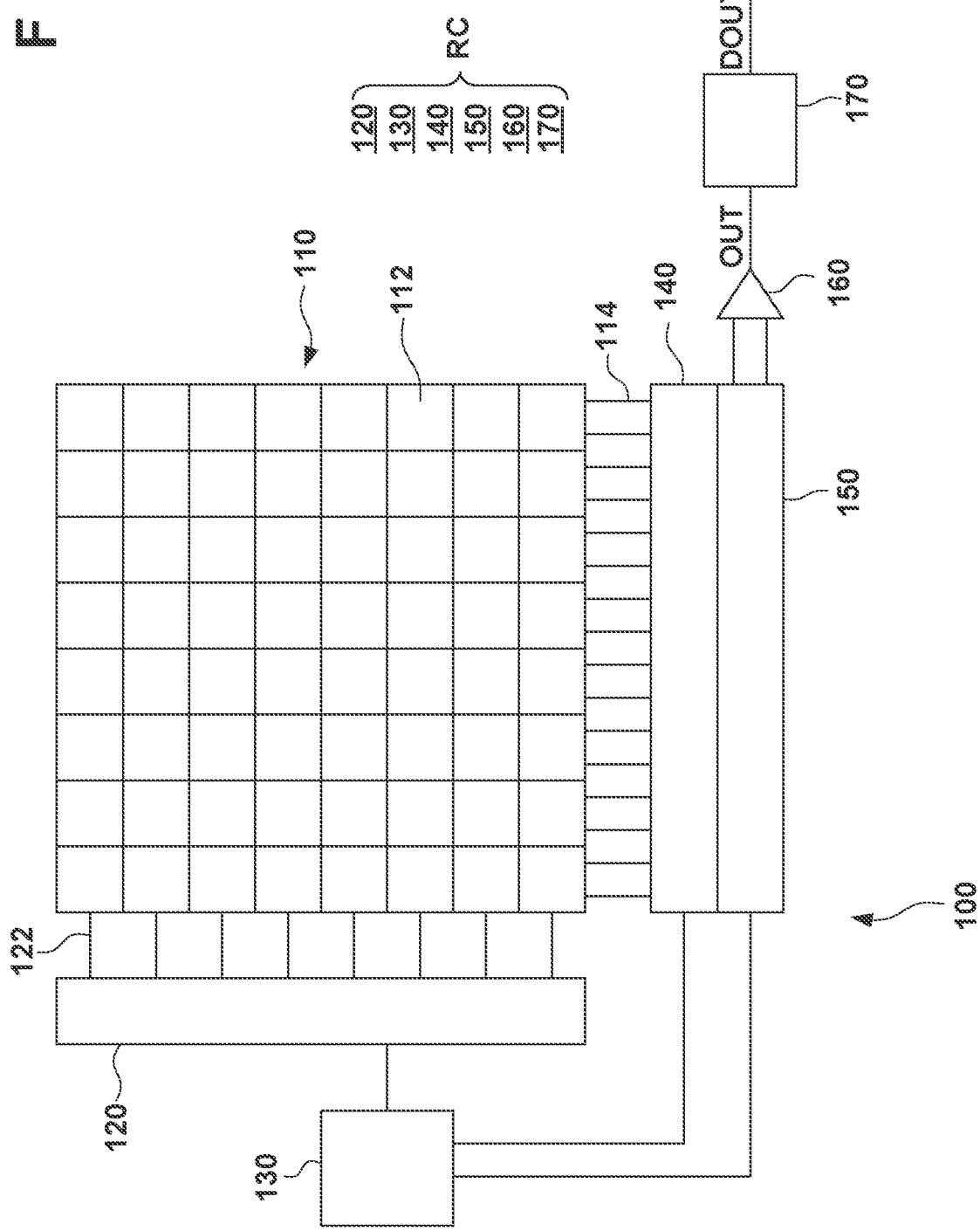
FIG. 2 is a block diagram showing an example of the configuration of an imaging unit.

FIG. 2 shows an example of the configuration of the imaging unit 100. As described above, the imaging unit 100 includes the pixel array 110 including a plurality of pixels 112, and a read circuit RC configured to read out signals from the plurality of pixels 112 of the pixel array 110. The plurality of pixels 112 can be arrayed to form a plurality of rows and a plurality of columns. The read circuit RC can include a row selection circuit 120, a timing generator (also called a control unit or a state machine) 130, a buffer circuit 140, a column selection circuit 150, an amplification unit 160, and an AD converter 170.

The row selection circuit 120 selects a row of the pixel array 110. The row selection circuit 120 can be configured to select a row by driving a row control signal 122. The buffer circuit 140 buffers signals from the pixels 112 of the row selected by the row selection circuit 120 from the plurality of rows of the pixel array 110. The buffer circuit 140 buffers the signals of a plurality of columns output to a plurality of column signal transmission paths 114 of the pixel array 110. The column signal transmission path 114 of each column includes a first signal line and a second signal line, which constitute a column signal line pair. A radiation signal according to the noise level of the pixel 112 or radiation detected in the pixel 112 can be output to the first column signal line. A radiation signal according to radiation detected in the pixel 112 can be output to the second column signal line. The buffer circuit 140 can include an amplification circuit.

The column selection circuit 150 selects, in a predetermined order, signal pairs of one row buffered by the buffer circuit 140. The amplification unit 160 amplifies the signal pairs selected by the column selection circuit 150. Here, the amplification unit 160 can be configured as a differential amplifier that amplifies the difference between a signal pair (two signals). The AD converter 170 AD-converts a signal OUT output from the amplification unit 160 and outputs a digital signal DOUT (radiation image signal).

Figure 3:
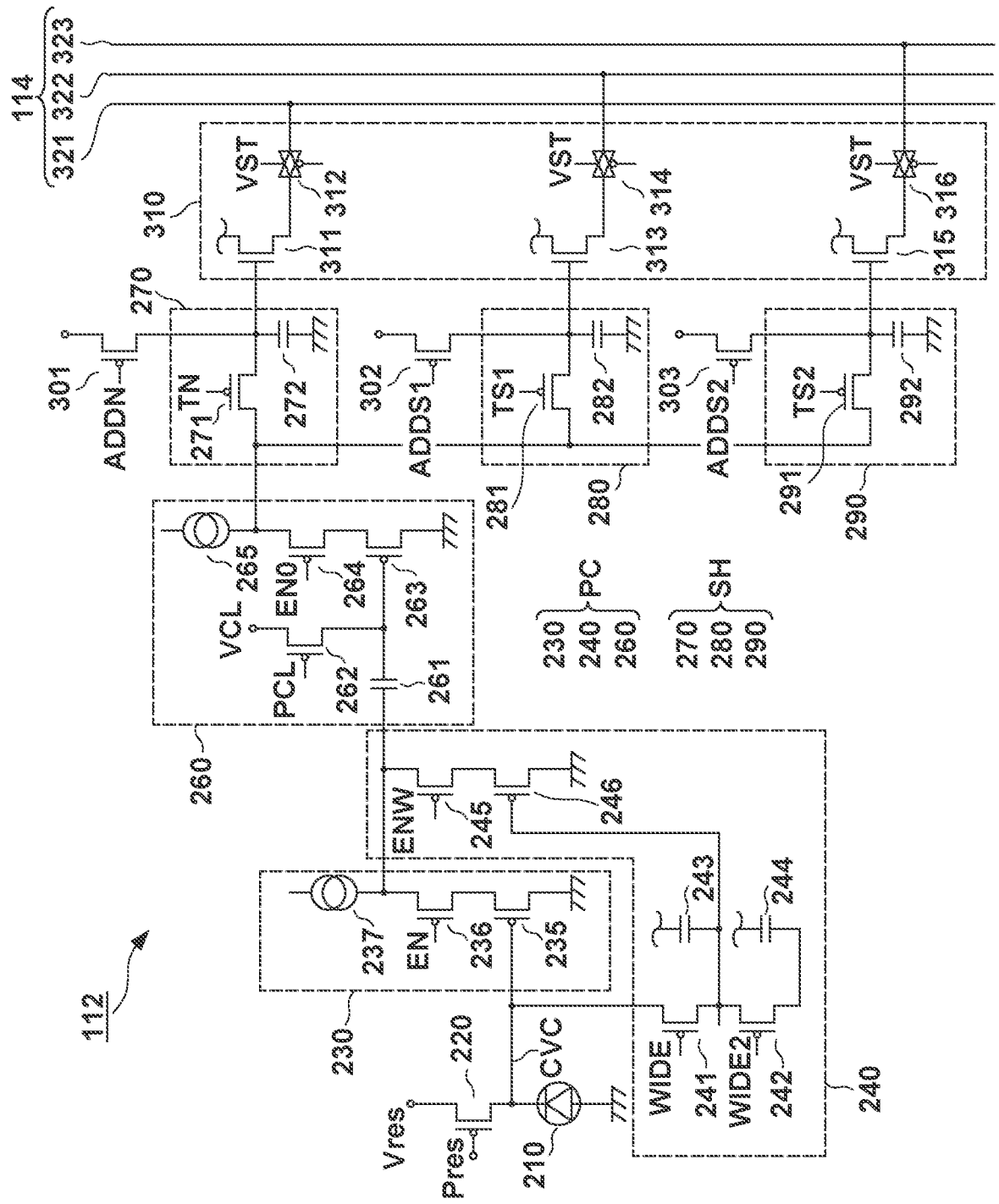
FIG. 3 is a circuit diagram showing an example of the configuration of one pixel.

FIG. 3 shows an example of the configuration of one pixel 112. The pixel 112 can include, for example, a conversion element 210, a processing circuit PC that processes an electrical signal output from the conversion element 210, and a holding unit SH that samples and holds the electrical signal output from the processing circuit PC. In addition, the pixel 112 can include a reset switch 220 (reset unit) that resets the conversion element 210, and an output circuit 310 that outputs the signal processed by the processing circuit PC. The processing circuit PC can include, for example, an amplification circuit 230, a sensitivity change unit 240, a clamp circuit 260, and sample hold circuits 270, 280, and 290.

The conversion element 210 converts radiation into an electrical signal. The conversion element 210 can be formed by, for example, a scintillator that can be shared by a plurality of pixels, and a photoelectric conversion element. The conversion element 210 includes a charge accumulation portion that accumulates a converted electrical signal (charges), that is, an electrical signal according to radiation. The charge accumulation portion is connected to the input terminal of the amplification circuit 230.

The amplification circuit 230 can include, for example, MOS transistors 235 and 236 and a current source 237. The MOS transistor 235 can be connected to the current source 237 via, for example, the MOS transistor 236. A source follower circuit can be formed by the MOS transistor 235 and the current source 237. The MOS transistor 236 can be an enable switch that is turned on by activating an enable signal EN and sets the source follower circuit formed by the MOS transistor 235 and the current source 237 in an operation state.

The charge accumulation portion of the conversion element 210 and the gate of the MOS transistor 235 can function as a charge/voltage conversion unit CVC that converts charges accumulated in the charge accumulation portion into a voltage. That is, a voltage V (=Q/C) determined by charges Q accumulated in the charge accumulation portion and a capacitance value C held by the charge/voltage conversion unit can appear in the charge/voltage conversion unit CVC. The charge/voltage conversion unit CVC can be connected to a reset potential Vres via the reset switch 220. When a reset signal PRES is activated, the reset switch 220 can be turned on to reset the potential of the charge/voltage conversion unit to the reset potential Vres. The reset switch 220 can include a transistor including a first main electrode (drain) connected to the charge accumulation portion of the conversion element 210, a second main electrode (source) to which the reset potential Vres is given, and a control electrode (gate). When an ON voltage is given to the control electrode, the transistor can reset the charge accumulation portion of the conversion element 210 by electrically connecting the first main electrode and the second main electrode.

The clamp circuit 260 can clamp, by a clamp capacitor 261, a reset noise level output from the amplification circuit 230 in accordance with the reset potential of the charge/voltage conversion unit CVC. The clamp circuit 260 can be configured to cancel the reset noise level from the signal (radiation signal) output from the amplification circuit 230 in accordance with the charges (electrical signal) converted by the conversion element 210. The reset noise level can include kTC noise upon resetting the charge/voltage conversion unit CVC. The clamp operation can be performed by activating a clamp signal PCL to turn on a MOS transistor 262 and, after that, inactivating the clamp signal PCL to turn off the MOS transistor 262.

The output side of the clamp capacitor 261 can be connected to the gate of a MOS transistor 263. The source of the MOS transistor 263 can be connected to a current source 265 via a MOS transistor 264. A source follower circuit can be formed by the MOS transistor 263 and the current source 265. The MOS transistor 264 can be an enable switch that is turned on by activating an enable signal ENO supplied to its gate and sets the source follower circuit formed by the MOS transistor 263 and the current source 265 in an operation state.

The output circuit 310 can include MOS transistors 311, 313, and 315, and row selection switches 312, 314, and 316. The MOS transistors 311, 313, and 315 can form source follower circuits together with current sources (not shown) connected to column signal lines 321, 322, and 323.

The radiation signal that is the signal output from the clamp circuit 260 in accordance with the charges generated in the conversion element 210 can be sampled and held (held) by the holding unit SH. The holding unit SH can include, for example, the first sample hold circuit 280 and the second sample hold circuit 290. The holding unit SH may also include the third sample hold circuit 270.

The radiation signal that is the signal output from the clamp circuit 260 in accordance with the charges generated in the conversion element 210 can be sampled and held (held) by the first sample hold circuit 280 at a first timing during a period in which the energy (wavelength) of radiation emitted from the radiation source 400 is increasing. The first sample hold circuit 280 can include a switch 281 and a capacitor 282. The switch 281 is turned on when a sample hold signal TS1 is activated. The radiation signal output from the clamp circuit 260 can be written in the capacitor 282 via the switch 281 when the sample hold signal TS1 is activated.

The radiation signal that is the electrical signal output from the clamp circuit 260 in accordance with the charges generated in the conversion element 210 can be sampled and held (held) by the second sample hold circuit 290 at a second timing. The second sample hold circuit 290 can include a switch 291 and a capacitor 292. The switch 291 is turned on when a sample hold signal TS2 is activated. The radiation signal (second signal) output from the clamp circuit 260 is written in the capacitor 292 via the switch 291 when the sample hold signal TS2 is activated. The holding unit SH may further include an additional sample hold circuit configured to write the radiation signal.

In a state in which the potential of the charge/voltage conversion unit CVC is reset by the reset switch 220, and the MOS transistor 262 is ON, the clamp circuit 260 outputs the noise level (offset component) of the clamp circuit 260. The noise level of the clamp circuit 260 can be sampled and held (held) by the third sample hold circuit 270. The sample hold circuit 270 can include a switch 271 and a capacitor 272. The switch 271 is turned on when a sample hold signal TN is activated. The noise level output from the clamp circuit 260 is written in the capacitor 272 via the switch 271 when the sample hold signal TN is activated. Also, in this embodiment, the sample hold circuit 270 (second signal holding unit) can also be used to hold the radiation signal that is the signal output from the clamp circuit 260 in accordance with the charges generated in the conversion element 210.

When a row selection signal VST is activated, signals according to the signals held by the sample hold circuits 270, 280, and 290 can be output from the output circuit 310 to the column signal lines 321, 322, and 323 that constitute the column signal transmission path 114. More specifically, an electrical signal N according to the electrical signal (noise level) held by the third sample hold circuit 270 can be output to the column signal line 321 via the MOS transistor 311 and the row selection switch 312. In addition, a signal S1 according to the electrical signal held by the first sample hold circuit 280 can be output to the column signal line 322 via the MOS transistor 313 and the row selection switch 314. Also, an electrical signal S2 according to the electrical signal (second radiation signal) held by the second sample hold circuit 290 can be output to the column signal line 323 via the MOS transistor 315 and the row selection switch 316.

The pixel 112 may include addition switches 301, 302, and 303 configured to add the signals of the plurality of pixels 112. In an addition mode, addition mode signals ADDN, ADDS1, and ADD2S are activated. When the addition mode signal ADDN is activated, the capacitors 272 of the plurality of pixels 112 can be connected to average the signals (noise levels). When the addition mode signal ADDS1 is activated, the capacitors 282 of the plurality of pixels 112 can be connected to average the signals. When the addition mode signal ADDS2 is activated, the capacitors 292 of the plurality of pixels 112 can be connected to average the signals.

The sensitivity change unit 240 of the processing circuit PC can include switches 241 and 242, capacitors 243 and 244, and MOS transistors 245 and 246. When a first change signal WIDE is activated, the switch 241 can be turned on to add the capacitance value of the first additional capacitor 243 to the capacitance value of the charge/voltage conversion unit CVC. This can lower the sensitivity of the pixel 112. Also, when a second change signal WIDE2 is also activated, the switch 242 can also be turned on to add the capacitance value of the second additional capacitor 244 to the capacitance value of the charge/voltage conversion unit CVC. This can further lower the sensitivity of the pixel 112. The dynamic range can be widened by adding the function of lowering the sensitivity of the pixel 112. If the first change signal WIDE is activated, an enable signal ENW may be activated. In this case, the MOS transistor 246 performs a source follower operation.

The above-described reset signal Pres, enable signal EN, clamp signal PCL, enable signal ENO, sample hold signals TN, TS1, and TS2, and row selection signal VST are control signals controlled by the row selection circuit 120 and correspond to the row control signal 122 in FIG. 2.

In the pixel 112 having the configuration shown in FIG. 3, signal destruction does not occur in the charge accumulation portion of the conversion element 210 and the like at the time of sample hold. That is, in the pixel 112 having the configuration shown in FIG. 3, the radiation signal can be read out nondestructively. This configuration is advantageous in radiation imaging using the energy subtraction method to be described below.

Figure 4:
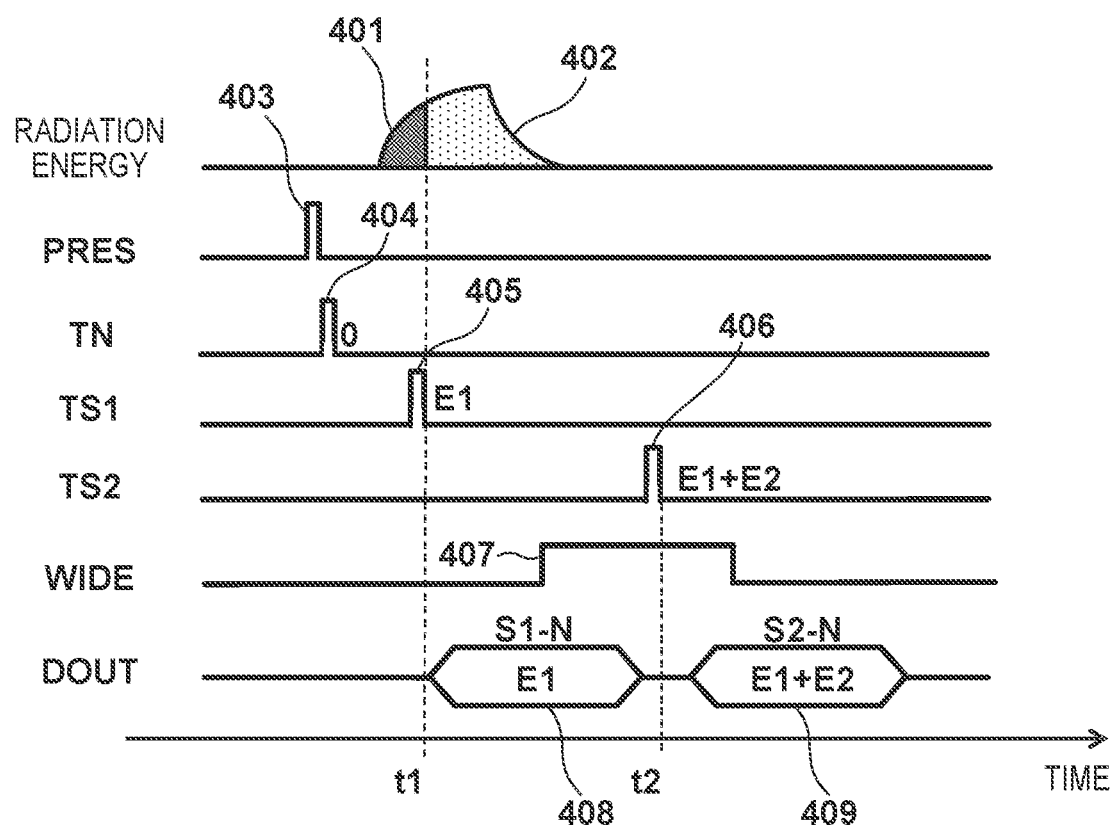
FIG. 4 is a timing chart showing an example of an operation according to the first embodiment.

FIG. 4 shows an operation example (image acquisition method) of the radiation imaging apparatus 1 when acquiring a radiation image by an energy subtraction method. In FIG. 4, the abscissa represents time. "Radiation energy" is the energy of radiation emitted from the radiation source 400 to irradiate the imaging unit 100. "PRES" is the reset signal PRES. "TS1" is the sample hold signal TS1. "WIDE" is the first change signal WIDE for changing the sensitivity (gain) of the processing circuit PC. The signal "DOUT" is the output of the AD converter 170. Synchronization between radiation emission from the radiation source 400 and the operation of the imaging unit 100 can be controlled by the control device 350. Operation control in the imaging unit 100 is done by the timing generator 130. During the period for activating the reset signal PRES, the clamp signal PCL is also activated for a predetermined period, and the noise level is clamped by the clamp circuit 260.

As shown in FIG. 4, the energy (wavelength) of radiation emitted from the radiation source 400 changes for the radiation emission period. This is because the rise and fall of the tube voltage of the radiation source 400 are dull (FIG. 4 shows an example in which radiation is emitted for a short period of several ms, and the energy always changes). That is, energy E1 of radiation 401 and energy E2 of radiation 402 can be different. Using this, a radiation image by the energy subtraction method can be obtained.

The operation of the radiation imaging apparatus 1 will be described below. In each pixel 112 of the radiation imaging apparatus 1, after radiation irradiation is started and before next radiation irradiation is started, the holding unit SH samples and holds an electrical signal output from the processing circuit PC at a first timing and a second timing, which are different from each other. Here, the first timing is a timing during the period in which the energy (wavelength) of the radiation emitted from the radiation source 400 is increasing. In addition, the sensitivity (gain) of the processing circuit PC at the first timing and the sensitivity (gain) of the processing circuit PC at the second timing are different from each other. The operation of each pixel 112 of the radiation imaging apparatus 1 will be described below in more detail.

Before radiation irradiation, the reset signal PRES is activated for a predetermined period, and this can reset the conversion element 210. At this time, the clamp signal PCL is also activated (not shown) for the predetermined period, and the reset level (noise level) can be clamped by the clamp circuit 260.

After the reset signal PRES is activated for the predetermined period, as indicated by reference numeral 403, the radiation source 400 can emit radiation in accordance with an exposure instruction from the exposure control device 300 to the radiation source 400. In an example, this operation can be done in the following way. First, the exposure switch of the exposure control device 300 is turned on. The exposure control device 300 notifies the control device 350 of this. In response to this, the control device 350 can output an instruction to the imaging unit 100 to start a series of operations (to be referred to as an imaging sequence hereinafter) for imaging. In response to this instruction, the imaging unit 100 can activate the reset signal PRES for the predetermined period as the operation at the start of the imaging sequence.

After the predetermined period elapses from the activation of the reset signal PRES for the predetermined period, the sample hold signal TN can be activated for a predetermined period, as indicated by reference numeral 404. Hence, a signal (0) of the pixel 112 in a radiation non-irradiation state can be sampled and held by the third sample hold circuit 270.

According to the start of the imaging sequence by the imaging unit 100, the control device 350 can output an instruction for starting radiation emission to the radiation source 400 via the exposure control device 300. In response to this, the radiation source 400 can start radiation emission.

After the predetermined period elapses from the activation of the sample hold signal TN for the predetermined period, as indicated by reference numeral 404, and the radiation source 400 starts radiation emission, the sample hold signal TS1 can be activated for a predetermined period, as indicated by reference numeral 405. Hence, an electrical signal (first component=E1) according to an electrical signal generated by the conversion element 210 of the pixel 112 upon receiving the irradiation of radiation with the energy E1 can be sampled and held by the first sample hold circuit 280.

After the predetermined period elapses from the activation of the sample hold signal TS1 for the predetermined period, as indicated by reference numeral 405, a first change signal 407 can be activated for a predetermined period. This switches the processing circuit PC to a low sensitivity (gain). Furthermore, during the activation period of the first change signal WIDE and after the irradiation of the radiation with the energy E2, the sample hold signal TS2 is activated for a predetermined period, as indicated by reference numeral 406. Hence, an electrical signal (first component+second component=E1+E2) according to an electrical signal generated by the conversion element 210 upon receiving the irradiation of the radiation 401 with the energy E1 and the radiation 402 with the energy E2 is sampled and held by the second sample hold circuit 290.

Here, the sample hold of the electrical signal including the first component (E1) by the first sample hold circuit 280 is completed at a first timing t1. In other words, the first sample hold circuit 280 samples and holds the electrical signal including the first component (E1) at the first timing t1. The sample hold of the electrical signal including the first component (E1) and the second component (E2) by the second sample hold circuit 290 is completed at a second timing t2. In other words, the second sample hold circuit 290 samples and holds the electrical signal including the first component (E1) and the second component (E2) at the second timing t2. Between the first timing t1 and the second timing t2, the first change signal WIDE is activated, and the sensitivity (gain) of the processing circuit PC is changed.

Next, an electrical signal corresponding to the difference between the electrical signal (0) sampled and held by the third sample hold circuit 270 and the electrical signal (E1) sampled and held by the first sample hold circuit 280 is output as a first electrical signal 408 from the read circuit RC. Subsequently, an electrical signal corresponding to the difference between the electrical signal (0) sampled and held by the third sample hold circuit 270 and the electrical signal (E1+E2) sampled and held by the second sample hold circuit 290 is output as a second electrical signal 409 from the read circuit RC.

Note that in FIG. 4, "N" represents an electrical signal sampled and held by the third sample hold circuit 270 and output to the first column signal line 321. "S1" represents an electrical signal sampled and held by the first sample hold circuit 280 and output to the second column signal line 322. "S2" represents an electrical signal sampled and held by the second sample hold circuit 290 and output to the second column signal line 322. The electrical signal (0) sampled and held by the third sample hold circuit 270 is a noise component and is not always zero. Such a noise component can similarly be included in the signal sampled and held by the first sample hold circuit 280. Hence, when the difference between the electrical signal sampled and held by the first sample hold circuit 280 and the electrical signal (0) sampled and held by the third sample hold circuit 270 is calculated, the noise component can be canceled. This is shown as E1−0=E1 in FIG. 4 for the sake of convenience. By repeating the above-described operation a plurality of times, radiation images of a plurality of frames (that is, a moving image) can be obtained.

The signal processing unit 352 can obtain the first electrical signal 408 (E1) and the electrical signal 409 (E1+E2) in the above-described way. Signal acquisition in a wide dynamic range can be performed by changing the sensitivity (gain) of the processing circuit PC between the sample hold of the first electrical signal and the sample hold of the second electrical signal. More specifically, the value of the first electrical signal readily becomes insufficient because the energy of radiation is low, and the irradiation time is short. However, the value of the first electrical signal can be made high by acquiring the signal at a high sensitivity. The value of the second electrical signal readily becomes excessive because the energy of radiation is high, and the irradiation time is long. However, the value of the second electrical signal can be made low by acquiring the signal at a low sensitivity. This can suppress shortage and excess of the signal amounts and obtain a sub-image suitable for energy subtraction.

Based on the first electrical signal 408 and the second electrical signal 409, the signal processing unit 352 can obtain an irradiation amount e1 of the radiation 401 with the energy E1 and an irradiation amount e2 of the radiation 402 with the energy E2. More specifically, the signal processing unit 352 can obtain the irradiation amount e2 of the radiation 402 with the energy E2 by calculating the first electrical signal (E1) and the second electrical signal (E1+E2). Note that when obtaining the irradiation amount e2 by calculation, the sensitivity at the time of sample hold can be taken into consideration. For example, if the sensitivity ratio of the processing circuit PC before and after the activation of the first change signal WIDE is (before activation:after activation=1:α), the first electrical signal can be subtracted from a value obtained by dividing the value of the second electrical signal by α. Alternatively, a value obtained by multiplying the value of the first electrical signal by a can be subtracted from the second electrical signal. The value α may uniformly be given to all pixels based on the design value of the capacitor 243, or may be given on a pixel basis in consideration of the variation of the capacitor 243. The value α of each pixel can be obtained from output information or the like before and after the change of the sensitivity.

Figure 5:
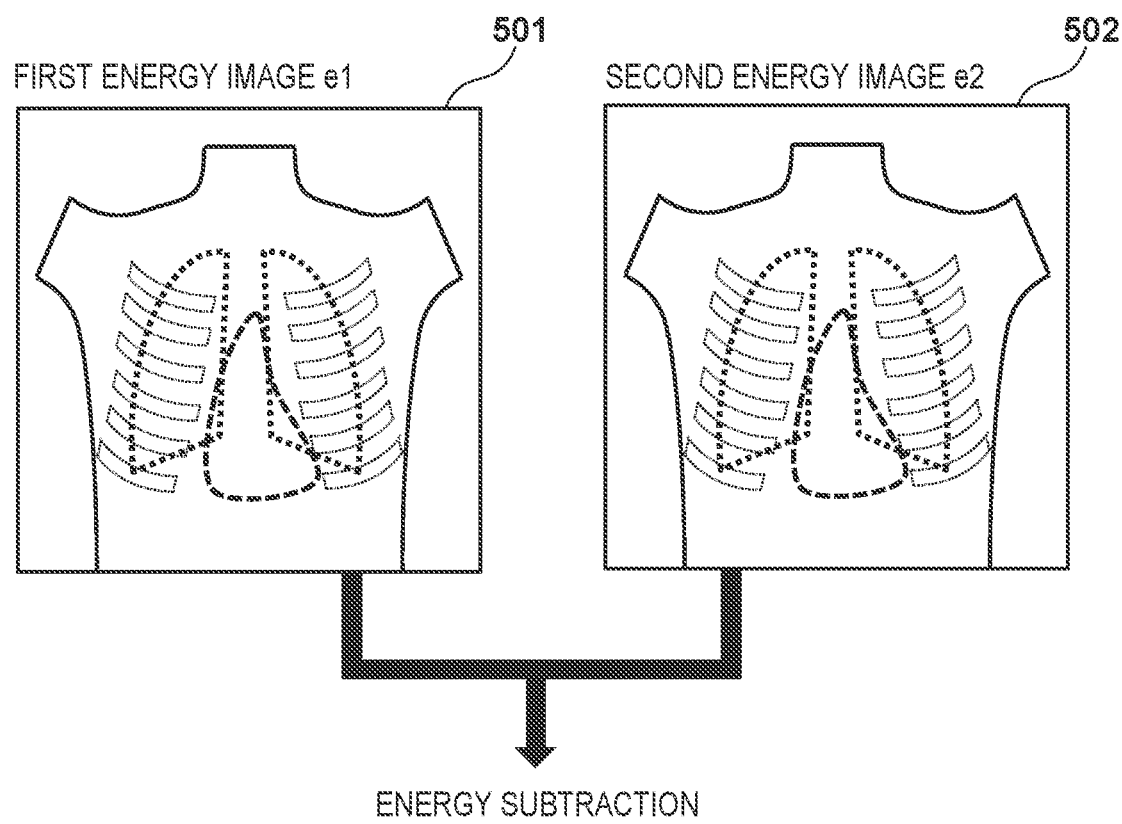
FIG. 5 is a view showing images obtained in the first embodiment.

Hence, as schematically shown in FIG. 5, the signal processing unit 352 can generate an image 501 of the irradiation amount e1 of the radiation 401 with the energy E1 and an image 502 of the irradiation amount e2 of the radiation 402 with the energy E2. As shown in FIG. 5, the signal processing unit 352 can perform energy subtraction using each of the images 501 and 502 as a sub-image.

Figure 6:
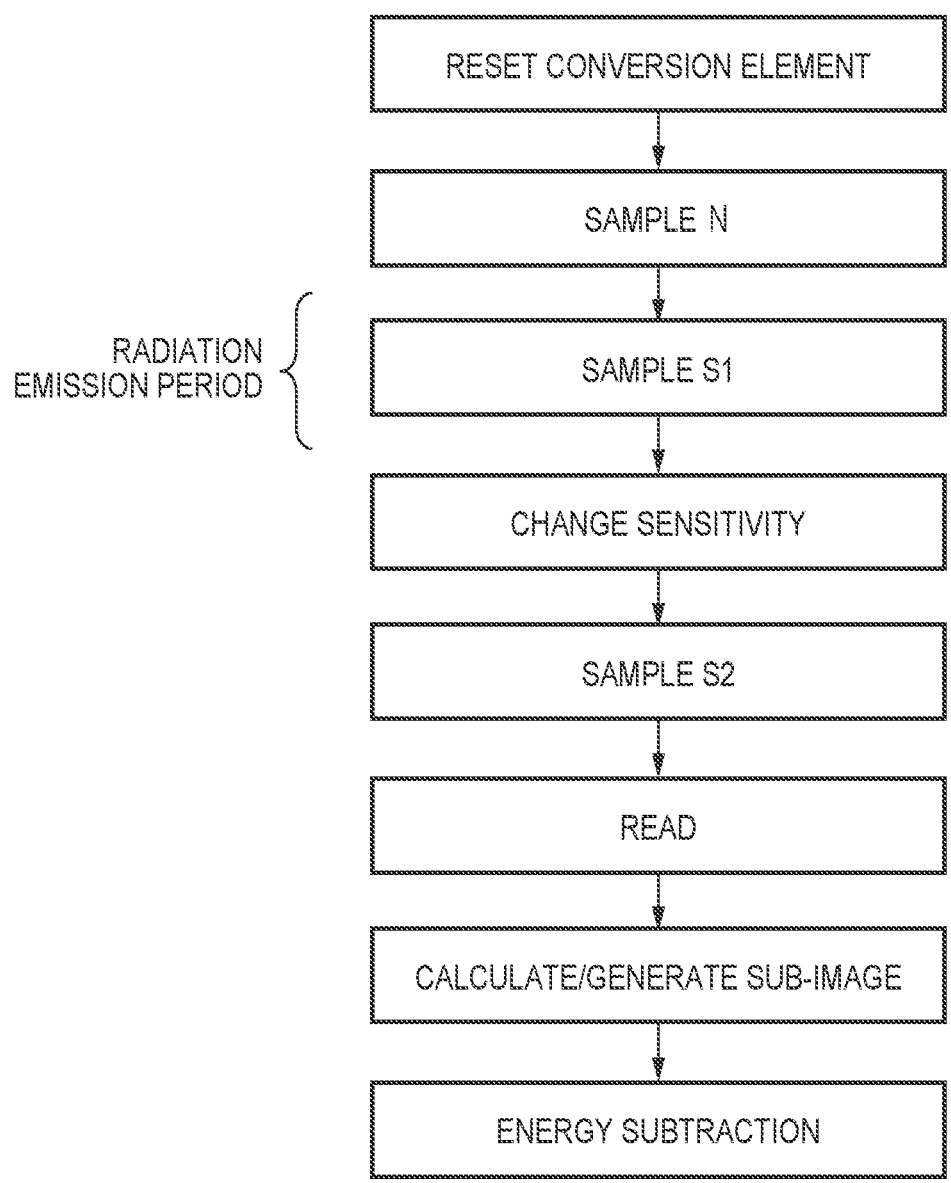
FIG. 6 is a flowchart showing the operation according to the first embodiment.

FIG. 6 shows the procedure of the operation from the reset operation of the conversion element 210 to the energy subtraction in the radiation imaging apparatus 1. The method of energy subtraction can be selected from various methods. For example, the difference between the radiation image of first energy and the radiation image of second energy is calculated, thereby obtaining an image in which a specific substance is enhanced. Alternatively, bone images and soft tissue images may be generated by solving nonlinear simultaneous equations based on the radiation image of the first energy and the radiation image of the second energy. Contrast agent images and soft tissue images can also be obtained based on the radiation image of the first energy and the radiation image of the second energy. In addition, electron density images and effective atomic number images can also be obtained based on the radiation image of the first energy and the radiation image of the second energy.

A form in which energy subtraction is performed based on two radiation images obtained by temporally dividing radiation into two energy bands has been described with reference to FIG. 4. However, the present invention is not limited to this form.

Figure 7:
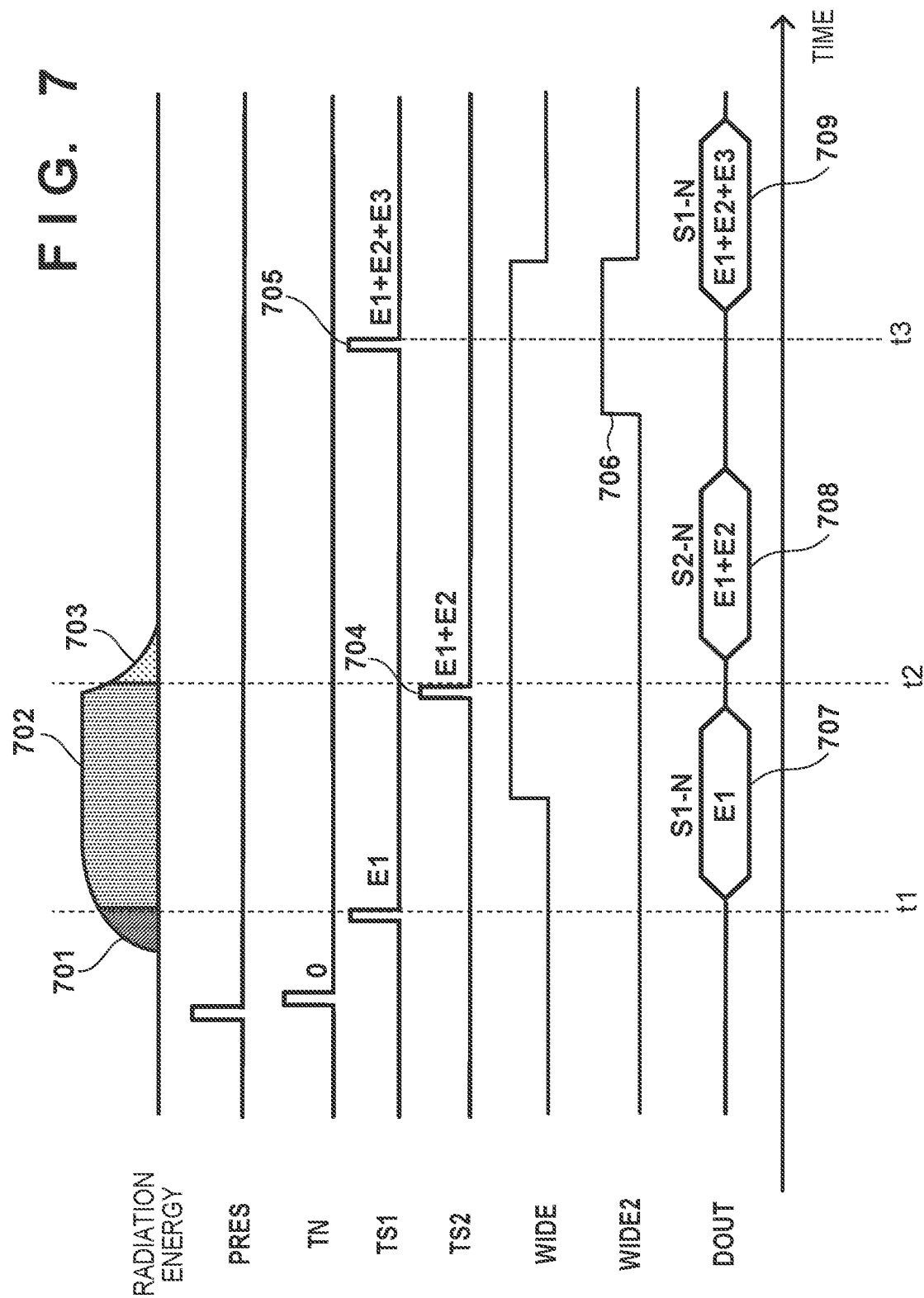
FIG. 7 is a timing chart showing another example of the operation according to the first embodiment.

FIG. 7 shows an example in which continuous radiation is divided into three energy bands, that is, radiation 701 in a rise period, radiation 702 in a stabilization period, and radiation 703 in a fall period. The radiation irradiation period in the example shown in FIG. 7 is longer than the radiation irradiation period in the example shown in FIG. 4. Referring to FIG. 7, "WIDE2" is the second change signal WIDE2 for changing the sensitivity (gain) of the processing circuit PC. The operation until a first electrical signal 707 and a second electrical signal 708 are output is the same as the operation until the output of the first electrical signal 408 and the second electrical signal 409 in FIG. 4, and a description thereof will be omitted.

After the sample hold signal TS2 is activated for a predetermined period, as indicated by reference numeral 704, and the predetermined period elapses, the second change signal WIDE2 can be activated for a predetermined period, as indicated by reference numeral 706. Hence, both the first change signal WIDE and the second change signal WIDE2 are set in the active state, and the sensitivity of the processing circuit PC can be changed to a lower sensitivity. During the period in which the first change signal WIDE and the second change signal WIDE2 are activated and after the end of irradiation of radiation with energy E3, the sample hold signal TS1 can be activated for a predetermined period, as indicated by reference numeral 705. Hence, an electrical signal (first component+second component+third component=E1+E2+E3) according to an electrical signal generated by the conversion element 210 upon receiving the irradiation of the radiations 701, 702, and 703 with the energies E1, E2, and E3 is sampled and held by the sample hold circuit 280.

Here, the sample hold of the electrical signal including the first component (E1) by the first sample hold circuit 280 is completed at the first timing t1. In other words, the first sample hold circuit 280 samples and holds the electrical signal including the first component (E1) at the first timing t1. The sample hold of the electrical signal including the first component (E1) and the second component (E2) by the second sample hold circuit 290 is completed at the second timing t2. In other words, the second sample hold circuit 290 samples and holds the electrical signal including the first component (E1) and the second component (E2) at the second timing t2. The sample hold of the electrical signal including the first component (E1), the second component (E2), and the third component (E3) by the first sample hold circuit 280 is completed at a third timing t3. In other words, the first sample hold circuit 280 samples and holds the electrical signal including the first component (E1), the second component (E2), and the third component (E3) at the third timing t3. The first component sampled and held by the first sample hold circuit 280 at the first timing t1 is output as a third electrical signal 709 from the read circuit RC before the start of next sample hold by the first sample hold circuit 280, which is completed at the third timing. Between the first timing t1 and the second timing t2, the first change signal WIDE is activated, and the sensitivity (gain) of the processing circuit PC is changed. Also, between the second timing t2 and the third timing t3, the second change signal WIDE2 is activated, and the sensitivity (gain) of the processing circuit PC is further changed.

Next, a signal corresponding to the difference between the electrical signal (0) sampled and held by the third sample hold circuit 270 and the electrical signal (E1+E2+E3) sampled and held by the first sample hold circuit 280 is output as the third electrical signal 709 from the read circuit RC.

The signal processing unit 352 can obtain the first electrical signal 707 (E1), the second electrical signal 708 (E1+E2), and the third electrical signal 709 (E1+E2+E3) in the above-described way. Based on the first electrical signal 707, the second electrical signal 708, and the third electrical signal 709, the signal processing unit 352 can obtain the irradiation amount e1 of the radiation 701 with the energy E1, the irradiation amount e2 of the radiation 702 with the energy E2, and an irradiation amount e3 of the radiation 703 with the energy E3. More specifically, the signal processing unit 352 can obtain the irradiation amount e2 of the radiation 702 with the energy E2 and the irradiation amount e3 of the radiation 703 with the energy E3 by calculating the first electrical signal (E1), the second electrical signal (E1+E2), and the third electrical signal (E1+E2+E3). Note that when obtaining the irradiation amounts e2 and e3 by calculation, the difference of the sensitivity at the time of sample hold can be taken into consideration, as in the configuration shown in FIG. 4.

The signal processing unit 352 may perform energy subtraction using three energy images or may perform energy subtraction using two images selected from the three images. Alternatively, a composite image may be generated from three energy images, and energy subtraction may be performed using two energy images. For example, energy subtraction can be performed using a low-energy image obtained by compositing the radiation 701 and the radiation 703 and a high-energy image based on the radiation 702. In the example shown in FIG. 7, the sensitivity is changed every time sample hold is performed. However, the change of the sensitivity is not limited to this.

Figure 8:
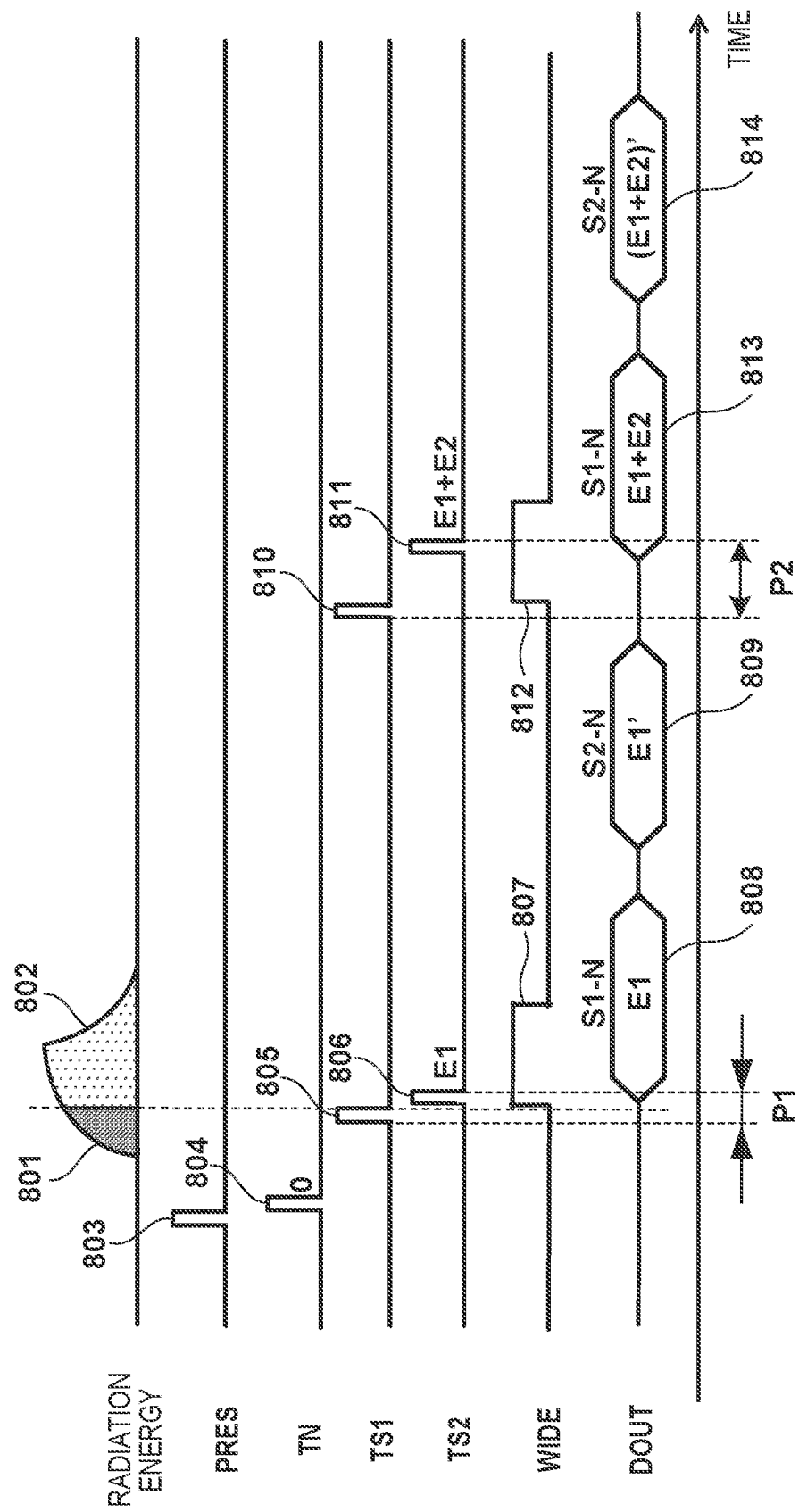
FIG. 8 is a timing chart showing an example of an operation according to the second embodiment.

A radiation imaging apparatus 1 according to the second embodiment of the present invention will be described below. Matters that are not mentioned in the second embodiment can comply with the first embodiment. FIG. 8 shows an operation example (image acquisition method) of the radiation imaging apparatus 1 when acquiring a radiation image by an energy subtraction method in the second embodiment.

Before radiation irradiation, a reset signal PRES is activated for a predetermined period, and this can reset a conversion element 210. At this time, a clamp signal PCL is also activated (not shown) for the predetermined period, and the reset level (noise level) can be clamped by a clamp circuit 260.

After the reset signal PRES is activated for the predetermined period, as indicated by reference numeral 803, a radiation source 400 can emit radiation in accordance with an exposure instruction from an exposure control device 300 to the radiation source 400. In an example, this operation can be done in the following way. First, the exposure switch of the exposure control device 300 is turned on. The exposure control device 300 notifies a control device 350 of this. In response to this, the control device 350 can output an instruction to an imaging unit 100 to start a series of operations (to be referred to as an imaging sequence hereinafter) for imaging. In response to this instruction, the imaging unit 100 can activate the reset signal PRES for the predetermined period as the operation at the start of the imaging sequence.

After the predetermined period elapses from the activation of the reset signal PRES for the predetermined period, a sample hold signal TN can be activated for a predetermined period, as indicated by reference numeral 804. Hence, a signal (0) of a pixel 112 in a radiation non-irradiation state can be sampled and held by a third sample hold circuit 270. According to the start of the imaging sequence by the imaging unit 100, the control device 350 can output an instruction for starting radiation emission to the radiation source 400 via the exposure control device 300. In response to this, the radiation source 400 can start radiation emission.

After the predetermined period elapses from the activation of the sample hold signal TN for the predetermined period, as indicated by reference numeral 804, and the radiation source 400 starts radiation, a sample hold signal TS1 can be activated for a predetermined period, as indicated by reference numeral 805. Hence, an electrical signal (E1) according to an electrical signal generated by the conversion element 210 of the pixel 112 upon receiving the irradiation of radiation with the energy E1 can be sampled and held by a first sample hold circuit 280.

After the sample hold signal TS1 is activated for the predetermined period, as indicated by reference numeral 805, a first change signal WIDE is activated for a predetermined period, as indicated by reference numeral 807. This changes a processing circuit PC to a low sensitivity (gain).

Furthermore, during the activation period of the first change signal WIDE, a sample hold signal TS2 is activated for a predetermined period, as indicated by reference numeral 806. Hence, a signal (E1') according to an electrical signal generated by the conversion element 210 of the pixel 112 upon receiving the irradiation of radiation 801 with the energy E1 and radiation 802 with energy E2 can be sampled and held by a second sample hold circuit 290. If the energy of radiation changes along with the elapse of time, as shown in FIG. 8, the activation of the first change signal WIDE (807) and the activation (806) of the sample hold signal TS2 are preferably performed immediately after the activation (805) of the sample hold signal TS1. This is because the larger the time difference between the activation (805) of the sample hold signal TS1 and the activation (806) of the sample hold signal TS2 is, the larger the difference between E1 and E1' is. The activation (805) of the sample hold signal TS1 and the activation (806) of the sample hold signal TS2 can be performed during a first period P1.

Next, an electrical signal corresponding to the difference between the electrical signal (0) sampled and held by the third sample hold circuit 270 and the electrical signal (E1) sampled and held by the first sample hold circuit 280 is output as an electrical signal 808 from the read circuit RC. Then, a signal corresponding to the difference between the electrical signal (0) sampled and held by the third sample hold circuit 270 and the signal (E1') sampled and held by the second sample hold circuit 290 is output as an electrical signal 809 from the read circuit RC.

After a predetermined period elapses from the activation of the sample hold signal TS1 for the predetermined period, as indicated by reference numeral 805, the sample hold signal TS1 can be activated for a predetermined period, as indicated by reference numeral 810. Hence, an electrical signal (E1+E2) according to an electrical signal generated by the conversion element 210 of the pixel 112 upon receiving the irradiation of the radiation 801 with the energy E1 and the radiation 802 with the energy E2 is sampled and held by the second sample hold circuit 290.

Next, the first change signal WIDE can be activated for a predetermined period, as indicated by reference numeral 812. This can change the processing circuit PC to a low sensitivity (gain). Furthermore, during the activation period of the first change signal WIDE and after the end of the irradiation of the radiation with the energy E2, the sample hold signal TS1 is activated for a predetermined period, as indicated by reference numeral 811. Hence, a signal ((E1+E2)') according to an electrical signal generated by the conversion element 210 of the pixel 112 upon receiving the irradiation of the radiation 801 with the energy E1 and the radiation 802 with the energy E2 is sampled and held by the second sample hold circuit 290. The activation (810) of the sample hold signal TS1 and the activation period (811) of the sample hold signal TS2 can be performed during a second period P2.

The first period P1 can be decided to be shorter than the period from the end of the first period P1 to the start of the second period P2. The second period P2 can be decided to be shorter than the period from the end of the first period P1 to the start of the second period P2. At a first timing in the first period P1, the first sample hold circuit 280 can sample and hold the first electrical signal 808. In addition, at a second timing in the first period P1, the second sample hold circuit 290 can sample and hold the second electrical signal 809. In other words, during the first period P1, a holding unit SH can sample electrical signals from the processing circuit PC at timings different from each other in a state in which the sensitivities (gains) of the processing circuit PC are different from each other. Also, during the second period P2, the holding unit SH can sample electrical signals from the processing circuit PC at timings different from each other in a state in which the sensitivities (gains) of the processing circuit PC are different from each other.

An electrical signal corresponding to the difference between the electrical signal (0) sampled and held by the third sample hold circuit 270 and the electrical signal (E1+E2) sampled and held by the first sample hold circuit 280 is output as an electrical signal 813 from the read circuit RC. Next, a signal corresponding to the difference between the electrical signal (0) sampled and held by the third sample hold circuit 270 and the electrical signal (E1'+E2') sampled and held by the second sample hold circuit 290 is output as an electrical signal 814 from the read circuit RC. By repeating the above-described operation a plurality of times, radiation images of a plurality of frames can be obtained.

The number of times of sample hold during the first period P1 and the number of times of sample hold during the second period P2 can be an arbitrary number. The number of times of sample hold during the first period P1 and the number of times of sample hold during the second period P2 may be different from each other. In the above-described way, a signal processing unit 352 can acquire the set of the electrical signals 808 (E1) and 809 (E1') processed at the sensitivities (gains) different from each other and the set of the electrical signals 813 (E1+E2) and 814 ((E1+E2)') processed at the sensitivities (gains) different from each other. Based on the electrical signals 808, 809, 813, and 814, the signal processing unit 352 can obtain an irradiation amount e1 of the radiation 801 with the energy E1 and an irradiation amount e2 of the radiation 802 with the energy E2. This method will exemplarily be described below.

Figure 9:
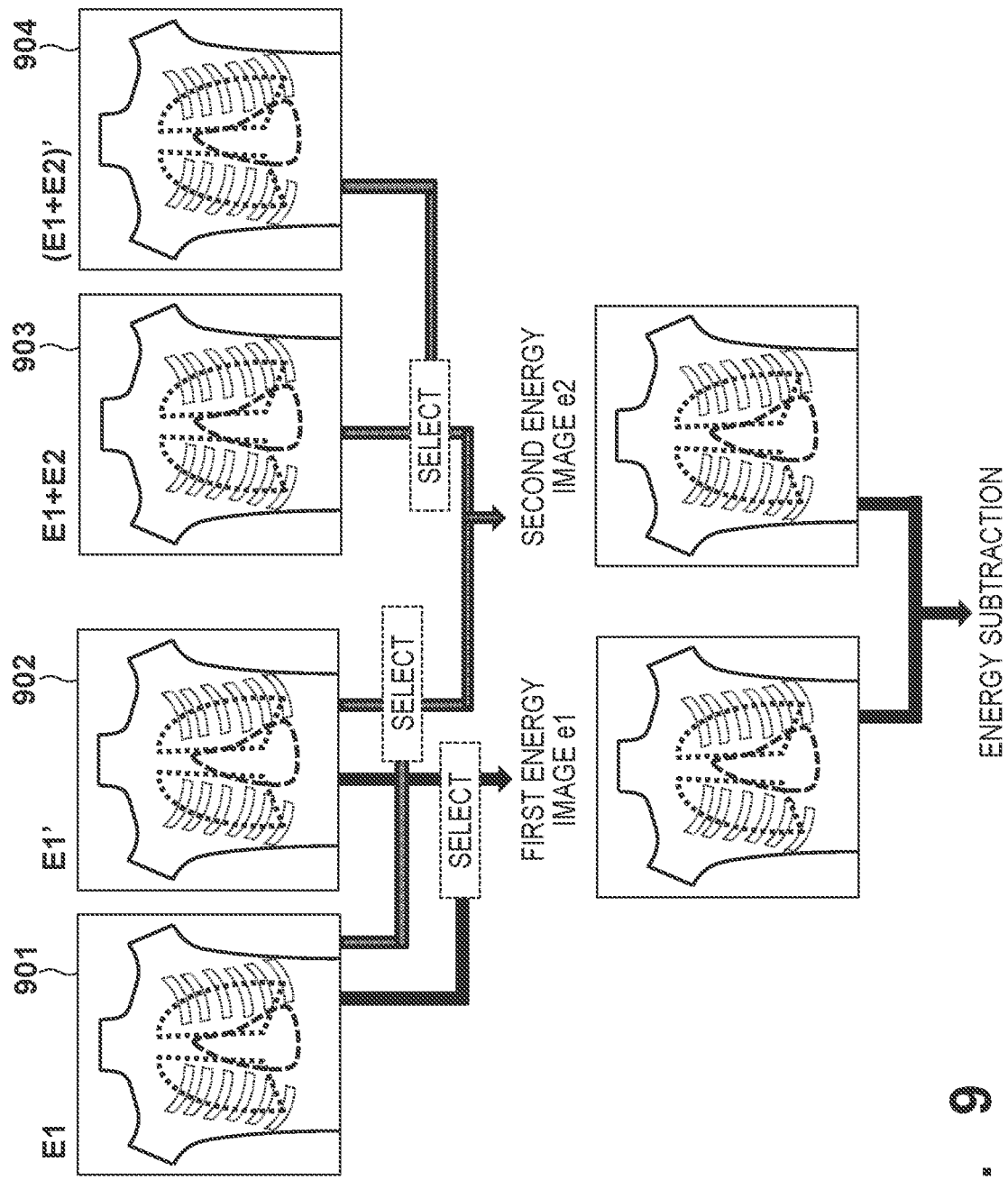
FIG. 9 is a view showing images obtained in the second embodiment.

As shown in FIG. 9, the image of the irradiation amount e1 of the radiation 801 with the energy E1, which is to be used in energy subtraction, can be selected from an image 901 based on the electrical signal 808 and an image 902 based on the electrical signal 809. Also, another image to be used in energy subtraction, that is, the image of the irradiation amount e2 of the radiation 802 with the energy E2 can be selected from an image 903 based on the electrical signal 813 and an image 904 based on the electrical signal 814. As for the image selection, for example, a threshold for evaluating the signal value in a specific region of an image is set, and the image selection can be done based on determination of the magnitude relationship between the threshold and the signal value in the specific region. The image selection may be performed on a pixel basis. The signal processing unit 352 can be configured, for example, as follows.

The signal processing unit 352 can generate a first image from a plurality of original images based on the electrical signal sampled and held during the first period P1, and generate a second image from a plurality of images based on the electrical signal sampled and held during the second period P2. Here, the first image is formed by a plurality of regions, and an original image that forms one region of the plurality of regions and an original image that forms another region of the plurality of regions can be different. In addition, the second image is formed by a plurality of regions, and an original image that forms one region of the plurality of regions and an original image that forms another region of the plurality of regions can be different. Selection of the original image that forms each of the plurality of regions can be done by, for example, determining the magnitude relationship between a pixel value of the original image and a threshold set for each of the plurality of regions. The signal processing unit 352 can generate a new image based on the first image and the second image. Alternatively, each of the plurality of regions may be formed by one pixel.

Alternatively, the signal processing unit 352 can generate the first image from a plurality of original images based on the electrical signal sampled and held during the first period P1, and generate the second image from a plurality of images based on the electrical signal sampled and held during the second period P2. In addition, the signal processing unit 352 may generate a third image based on the first image and the second image and generate a new image based on the first image and the third image. Here, the first image is formed by a plurality of regions, and an original image that forms one region of the plurality of regions and an original image that forms another region of the plurality of regions can be different. In addition, the second image is formed by a plurality of regions, and an original image that forms one region of the plurality of regions and an original image that forms another region of the plurality of regions can be different.

Figure 10:
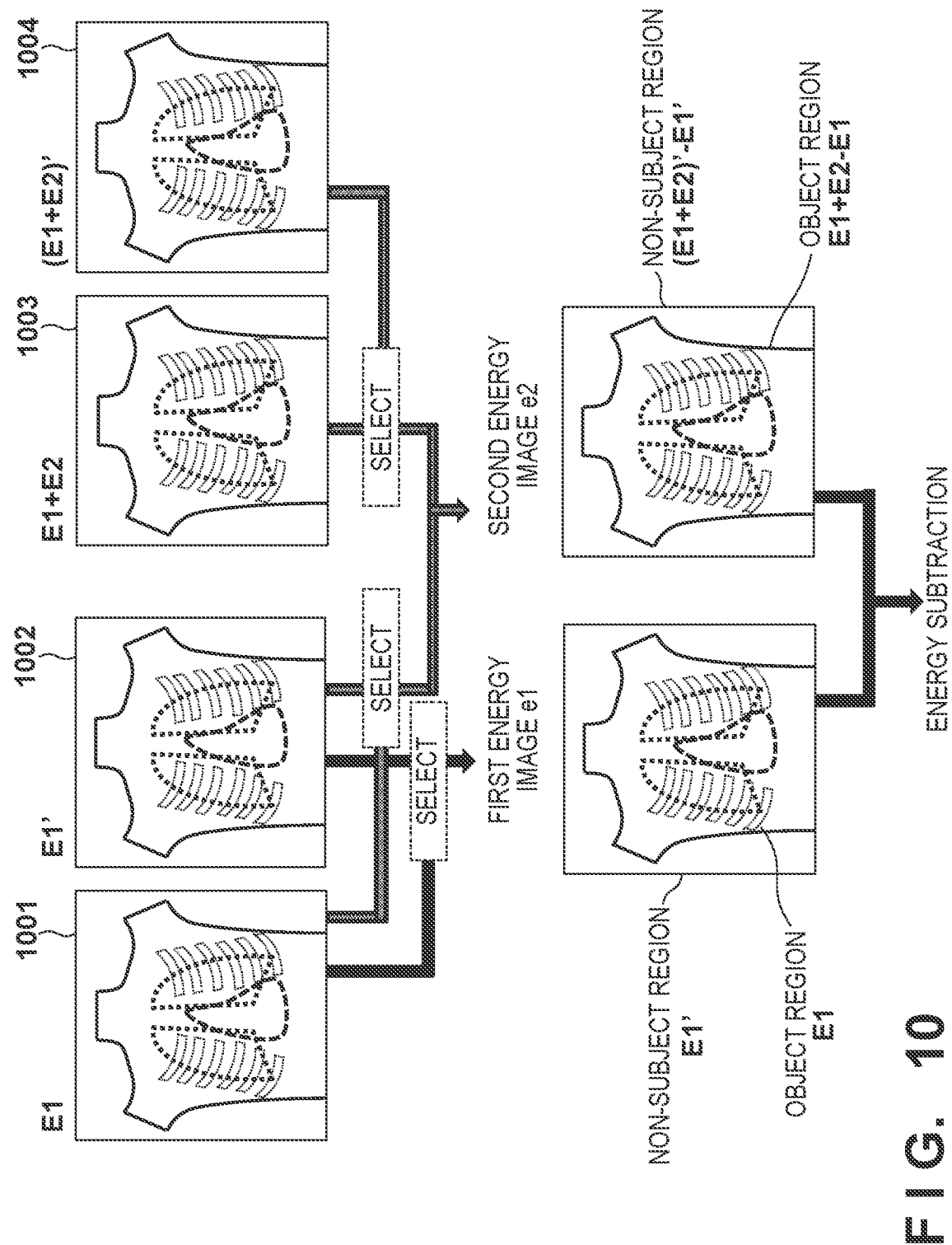
FIG. 10 is a view showing other images obtained in the second embodiment.

FIG. 10 exemplarily shows the above-described energy subtraction. An image 1001 is an image based on the electrical signal 808, and an image 1002 is an image based on the electrical signal 809. An image 1003 is an image based on the electrical signal 813, and an image 1004 is an image based on the electrical signal 814. Each of the images 1001 to 1004 includes an object region (a region where a subject exists) and a non-subject region (a region other than the object region).

Figure 11:
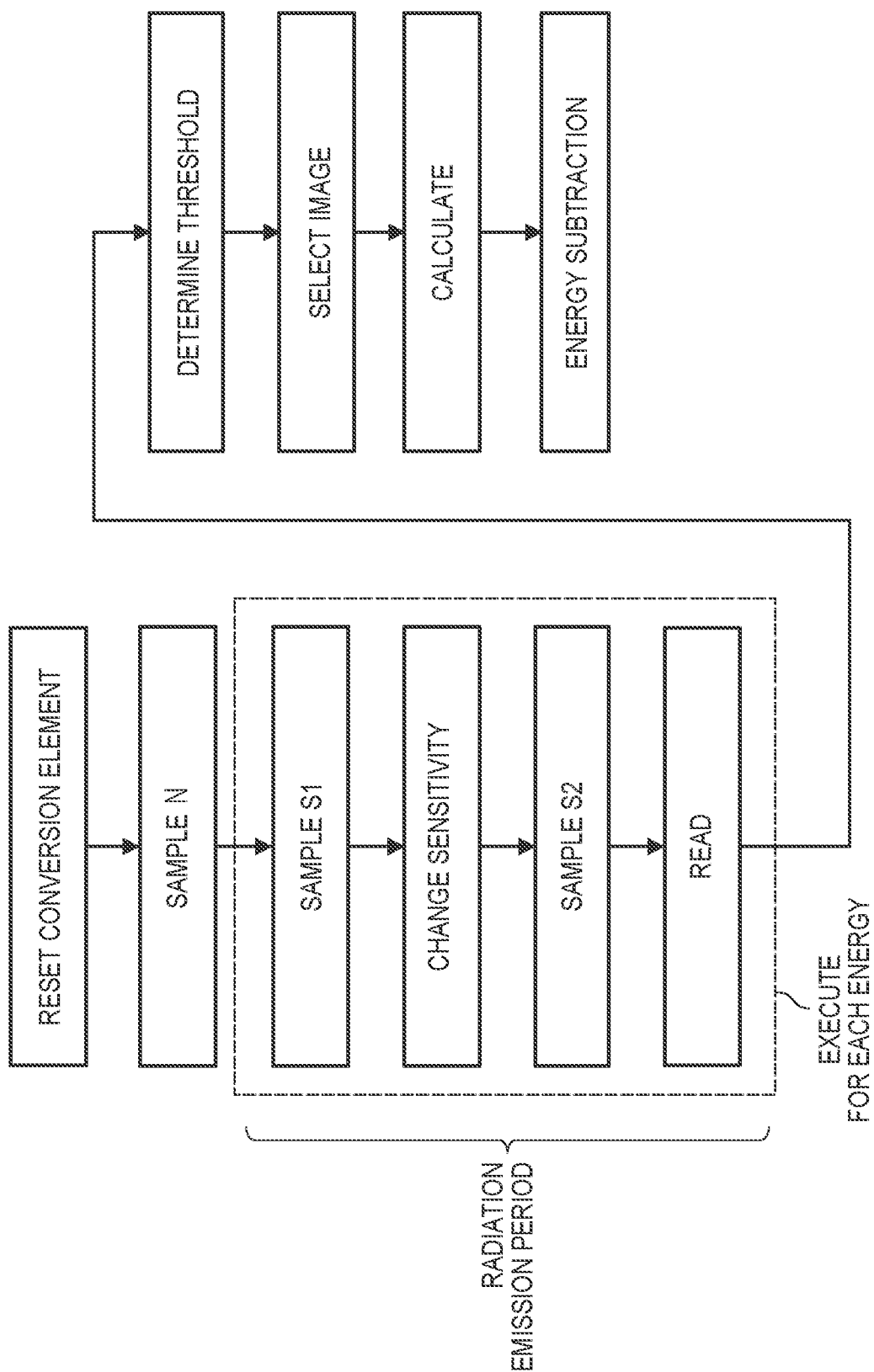
FIG. 11 is a flowchart showing the operation according to the second embodiment.

The signal processing unit 352 generates the image of the object region from the image 1001 (original image) and generates the image of the non-subject region from the image 1002 (original image), thereby generating a first energy image e1 as the first image. The signal processing unit 352 generates the image of the object region from the image 1003 (original image) and generates the image of the non-subject region from the image 1004 (original image), thereby generating the second image (not shown). Then, the signal processing unit 352 can generate a third energy image e2 as the third image based on the first image and the second image. Furthermore, the signal processing unit 352 can generate a new image (not shown) based on the first image and the third image. In another viewpoint, the signal processing unit 352 can generate an image based on two images generated from a plurality of images based on the electrical signal sampled and held during the first period and a plurality of images based on the electrical signal sampled and held during the second period. FIG. 11 shows the procedure of the operation from the reset operation of the conversion element 210 to the energy subtraction in the radiation imaging apparatus 1.

In the second embodiment, the plurality of images (original images) can be acquired by acquiring, for each energy band of radiation, images at a sensitivity according to the energy band. Also, in the second embodiment, an image (sub-image) for energy subtraction can be generated from the plurality of images (original images). This can acquire a sub-image in a wide dynamic range. Here, energy subtraction may be used to generate the sub-image. It is also possible to cope with a real-time change of the imaging environment (the SID, the radiation irradiation condition, and the like) by selecting the original image used to generate the sub-image in accordance with the signal value of a pixel (for example, the comparison result between a threshold and the signal value of a pixel).

The combination of sensitivities to be used when performing sample hold a plurality of times for each energy of radiation may be changed. For example, if sensitivities of three steps, that is, sensitivity 1, sensitivity 2, and sensitivity 3 can be set, the combination may be changed such that sample hold is performed using sensitivity 1 and sensitivity 2 in the first period, and sample hold is performed using sensitivity 2 and sensitivity 3 in the second period. In addition, the number of times of sample hold may be changed for each energy of radiation. Furthermore, the threshold used to select an original image for each energy of radiation can be determined arbitrarily.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus including an imaging unit having a plurality of pixels, wherein
each of the plurality of pixels includes a conversion element configured to convert radiation into an electrical signal, a processing circuit configured to process the electrical signal output from the conversion element, and a holding unit configured to sample and hold the electrical signal output from the processing circuit,
after radiation irradiation from a radiation source is started and before next radiation irradiation from the radiation source is started, the holding unit is configured to sample and hold, at a first timing, a second timing which is after the first timing, and a third timing which is after the second timing, the electrical signal output from the processing circuit, and
a gain of the processing circuit at the first timing, the gain of the processing circuit at the second timing, and the gain of the processing circuit at the third timing are different from each other.

2. The radiation imaging apparatus according to claim 1, wherein the first timing is a timing during a period in which energy of the radiation emitted from the radiation source is increasing, and
the holding unit is configured to output the electrical signal sampled and held at the first timing and the electrical signal sampled and held at the second timing.

3. The radiation imaging apparatus according to claim 1, further comprising a signal processing unit configured to process an electrical signal from the imaging unit, wherein
the electrical signal sampled and held by the holding unit at the first timing includes a first component, and the electrical signal sampled and held by the holding unit at the second timing includes a second component in addition to the first component, and
the signal processing unit performs signal processing of generating a radiation image by an energy subtraction method based on an image based on the electrical signal sampled and held at the first timing and an image based on the electrical signal sampled and held at the second timing.

4. The radiation imaging apparatus according to claim 1, wherein the holding unit is configured to output the electrical signal sampled and held at the first timing, the electrical signal sampled and held at the second timing, and the electrical signal sampled and held at the third timing.

5. The radiation imaging apparatus according to claim 1, wherein the electrical signal sampled and held by the holding unit at the first timing includes the first component, the electrical signal sampled and held by the holding unit at the second timing includes the second component in addition to the first component, and the electrical signal sampled and held by the holding unit at the third timing includes a third component in addition to the second component and the first component.

6. The radiation imaging apparatus according to claim 1, wherein the holding unit is configured to sample and hold the electrical signal output from the processing circuit a plurality of times in a first period,
the holding unit is configured to sample and hold the electrical signal output from the processing circuit the plurality of times in a second period after the first period,
the holding unit is configured to output the electrical signal sampled and held the plurality of times in the first period and the electrical signal sampled and held the plurality of times in the second period,
the first period is shorter than a period from an end of the first period to a start of the second period, and
the first timing and the second timing belong to the first period.

7. The radiation imaging apparatus according to claim 1, wherein the holding unit is configured to sample and hold the electrical signal output from the processing circuit a first number of times in a first period,
the holding unit is configured to sample and hold the electrical signal output from the processing circuit a second number of times in a second period after the first period, the second number of times being different from the first number of times,
the holding unit is configured to output the electrical signal sampled and held the first number of times in the first period and the electrical signal sampled and held the second number of times in the second period,
the first period is shorter than a period from an end of the first period to a start of the second period, and
the first timing and the second timing belong to the first period.

8. The radiation imaging apparatus according to claim 6, wherein the first period includes a period in which the radiation is emitted, and the second period does not include the period in which the radiation is emitted.

9. The radiation imaging apparatus according to claim 1, wherein the holding unit includes a first sample hold circuit configured to sample and hold, at the first timing and the third timing, the electrical signal output from the processing circuit, and a second sample hold circuit configured to sample and hold, at the second timing, the electrical signal output from the processing circuit.

10. The radiation imaging apparatus according to claim 9, wherein after the sample and hold by the first sample hold circuit, the sample and hold by the second sample hold circuit is executed, and
the electrical signal sampled and held by the first sample hold circuit includes the first component, and the electrical signal sampled and held by the second sample hold circuit includes the second component in addition to the first component.

11. The radiation imaging apparatus according to claim 9, wherein after the radiation irradiation is started and before the next radiation irradiation is started,
the first sample hold circuit is configured to sample and hold, at the first timing, the electrical signal output from the processing circuit, after that, the second sample hold circuit is configured to sample and hold, at the second timing, the electrical signal output from the processing circuit, after that, the first sample hold circuit is configured to sample and hold, at the third timing, the electrical signal output from the processing circuit, and after that, the second sample hold circuit is configured to sample and hold, at a fourth timing, the electrical signal output from the processing circuit.

12. The radiation imaging apparatus according to claim 11, wherein a time difference between the first timing and the second timing is smaller than a time difference between the second timing and the third timing,
the first timing and the second timing are timings included in a period in which the radiation is emitted, and the third timing and the fourth timing are timings after the period,
a time difference between the third timing and the fourth timing is smaller than the time difference between the second timing and the third timing, and
the time difference between the third timing and the fourth timing is larger than the time difference between the first timing and the second timing.

13. The radiation imaging apparatus according to claim 6, further comprising a signal processing unit configured to process an electrical signal from the imaging unit, wherein
the signal processing unit is configured to generate the radiation image based on an image selected from a plurality of images based on the electrical signal sampled and held the plurality of times in the first period and an image selected from a plurality of images based on the electrical signal sampled and held the plurality of times in the second period.

14. The radiation imaging apparatus according to claim 6, further comprising a signal processing unit configured to process an electrical signal from the imaging unit, wherein
the signal processing unit is configured to generate the radiation image based on two images generated from a plurality of images based on the electrical signal sampled and held in the first period and a plurality of images based on the electrical signal sampled and held in the second period.

15. An image acquisition method of acquiring a radiation image using a radiation imaging apparatus including an imaging unit with a plurality of pixels, each of the plurality of pixels a conversion element configured to convert radiation into an electrical signal, a processing circuit configured to process the electrical signal output from the conversion element, and a holding unit configured to sample and hold the electrical signal output from the processing circuit, the image acquisition method comprising:
a step of, after radiation irradiation from a radiation source is started and before next radiation irradiation from the radiation source is started, sampling and holding, by the holding unit at a first timing and a second timing which is after the first timing, and a third timing which is after the second timing, the electrical signal output from the processing circuit; and
a gain of the processing circuit at the first timing, the gain of the processing circuit at the second timing, and the gain of the processing circuit at the third timing are different from each other.

16. A non-transitory computer-readable storage medium storing a program for causing a computer to execute the method according to claim 15.

* * * * *